United States Patent [19]

Weinberger

[11] Patent Number: Plant 5,342

[45] Date of Patent: Nov. 20, 1984

[54] PLUM TREE, SUPLUMFOURTEEN

[75] Inventor: John H. Weinberger, Fresno, Calif.

[73] Assignee: Superior Farming Company, Bakersfield, Calif.

[21] Appl. No.: 465,675

[22] Filed: Feb. 10, 1983

[51] Int. Cl.[3] ..... A01H 5/00

[52] U.S. Cl. ..... Plt./38

[58] Field of Search ..... Plt./38

*Primary Examiner*—James R. Feyrer

*Attorney, Agent, or Firm*—Huebner & Worrel

[57] ABSTRACT

A new variety of plum tree bearing clingstone fruit having a reddish purple skin and ripening approximately with the Santa Rosa variety (unpatented), plums of the new variety having superior shipping and keeping qualities, having flesh which is less acid than that of the Santa Rosa variety and which attains a more fully reddish coloration when relatively immature, and having a somewhat longer ripening period than plums of the Santa Rosa variety.

1 Drawing Figure

BACKGROUND OF THE VARIETY

The present invention relates to a new and distinct variety of plum tree which has been named "Suplumfourteen" for commercial marketing. The new variety is broadly characterized by its general resemblance to the Santa Rosa variety of plum tree (unpatented), but distinguished therefrom by its fruit being of larger size, having a more purple skin coloration, having a relatively ovoid form with a relatively flattened and broader base, with shoulders slanted more toward the apex, and with an apex which is a rounded point rather than a depression. The present variety is further distinguished from the Santa Rosa variety by the present variety bearing fruit which attains a fully reddish flesh coloration when relatively immature, has a superior shipping and keeping quality, has flesh which is substantially less acid, and has a slower ripening quality so that fewer pickings are required and the marketing period is longer.

More fresh plums of the Santa Rosa variety are shipped commercially in the state of California than plums of any other variety due to such reasons as the attractive appearance and excellent flavor of plums of this popular variety. However, fruit of the Santa Rosa variety is deficient in that its flesh is highly acid and that its shipping and keeping quality is relatively poor. A slow ripening quality is desirable in fresh fruits, thereby extending the marketing period in that the fruit remains suitable for consumption over a longer period of time. It is desirable that fresh fruits attain their fully mature coloration early so that they may be harvested as soon as possible.

ORIGIN AND ASEXUAL REPRODUCTION OF THE NEW VARIETY

The subject variety of plum tree was discovered during a plant breeding program conducted by me for the Superior Farming Company, a corporation of Nevada. During this program, open pollinated seeds of the Angeleno variety of plum tree (U.S. Plant Pat. No. 2,747) were grown to fruition, and trees from such seeds showing desirable characteristics were, under my direction, selected and propagated by budding onto other trees or rootstocks. The subject variety was discovered on June 24, 1979. Upon asexual reproduction of the subject variety, as performed in that year, it was found the tree and fruit characteristics which resulted were identical to those of the one tree. The above-designated program, which resulted in the subject variety, was carried on in a breeding orchard owned by Superior Farming Company and located at 5090 East Church Avenue, near the City of Fresno, in the County of Fresno, and in the state of California.

SUMMARY OF THE NEW VARIETY

The subject variety of plum tree is similar to the Santa Rosa variety (unpatented) in that the varieties ripen at the same time, bear fruit having a purplish-reddish skin coloration and having pinkish or reddish flesh when fully ripe. However, plums of the subject variety are distinguished from those of the Santa Rosa variety in having a form which is somewhat ovoid, rather than globose, as in the Santa Rosa, and having a flatter, broader base and shoulders slanted more toward the apex, the apex of the subject variety being a short, rounded point rather than being depressed as in the Santa Rosa. The skin coloration of the subject variety is relatively more purple and less red than that of the Santa Rosa. Fruit of the subject variety is more particularly distinguished from that of the Santa Rosa variety by being 5-10 millimeters larger in diameter, by having flesh which acquires a fully red coloration from skin to stone when the fruit is relatively immature rather than being yellow until fully ripe as in the Santa Rosa, and by fruit of the subject variety having a slower ripening quality giving it a longer marketing period than fruit of the Santa Rosa variety. The subject variety is especially distinguished from the Sant Rosa variety in bearing plums having a superior keeping and shipping quality and having a flesh which is less acid.

BRIEF DESCRIPTION OF THE DRAWING

The accompanying drawing is a color photograph of plums borne by the subject variety, one of the plums being divided to show the stone and flesh characteristics, and the plums being depicted with a twig of the subject variety having characteristic leaves.

DETAILED DESCRIPTION

Referring more specifically to the subject variety of plum tree, the following is a horticultural description of characteristics thereof resulting from the growing conditions in the above-identified orchard located in the San Joaquin Valley of California. It is to be understood that variations of the usual magnitude incident to growing conditions, fertilization, pruning, and pest control are to be expected in such characteristics. In the following description, color plate references are to the "Plochere Color System", which is published in Los Angeles, Calif., common descriptive color terms also being employed.

DESCRIPTION

Harvest period:

*Date of first picking.*—June 16, 1980.

*Date of last picking.*—June 24, 1980.

DESCRIPTION OF THE VARIETY

Tree: Medium size, medium vigor, upright, dense, round topped, very productive, regular bearing.

Trunk: Medium size, medium texture.

Branches: Medium size; medium texture, brown in color with dull green new growth.

Leaves: Length 11.2 cm. Width 5.1 cm. Medium size, elliptical, pointed at both ends, acuminate, gradual point, medium thickness, medium green in color, smooth.

Margin: Crenate.

Petiole: Medium length, medium thickness.

Glands: Average number 2, opposite, small, globose, green in color.

*Position.*—Base of blade.

Stipules: Many still attached, up to 8 mm in length.

Flower buds: Medium size, medium length, pointed, free.

Flowers: Medium date of bloom compared with other varieties; full bloom, Mar. 1, 1982; medium size, white in color.

Fruit: Described when firm ripe on June 24, 1980; first picking June 16, 1980; last picking June 24, 1980.

*Size.*—Medium.

*Diameter.*—Axial, 52 mm; transverse in suture plane, 58 mm.

*Form.*—Uniform, symmetrical, narrowly ovoid.

*Suture.*—An inconspicuous line extending from base, but discontinued at apex.

*Ventral surface.*—Rounded.

*Lips.*—Equal.

*Cavity.*—Rounded, circular. Depth: 7 mm. Breadth: 14 mm. Markings: none.

*Base.*—Rounded.

*Apex.*—Short, rounded.

*Pistil point.*—Apical.

Skin: Medium thickness, medium tough, tenaciously to flesh.

*Tendency to crack.*—None in dry season.

*Color.*—Unpolished stem cavity — 397, Plate 17, "Rose Marie". Skin with bloom removed — 433, Plate 28, "Spectra Rose". Bloom — gray.

*Down.*—Wanting.

Flesh:

*Color.*—Red; surface of pit cavity, 386 Plate 17, "Fuchsia".

*Amygdalin.*—Wanting.

*Juice.*—Moderate.

*Texture.*—Firm, fine.

*Fibers.*—Few, fine.

*Ripens.*—Evenly.

*Flavor.*—Slightly acid, delicate.

*Aroma.*—Wanting.

*Eating quality.*—Superior.

Stone: Cling, adheres to flesh over entire surface.

*Fibers.*—Short.

*Size.*—Medium.

*Length.*—22 mm.

*Breadth.*—16 mm.

*Thickness.*—7 mm.

*Form.*—Elliptical.

*Base.*—Straight.

*Hilum.*—Oval.

*Apex.*—Rounded.

*Sides.*—Equal.

*Surface.*—Ridged throughout.

*Ridges.*—Jagged, interrupted.

*Ventral edge.*—Thin, without wing.

*Dorsal edge.*—Narrow, with narrow groove throughout.

*Color of stone.*—171, "French Yellow".

*Tendency to split.*—Slight in dry season.

Use: Market.

Keeping quality: Good.

Shipping quality: Good.

Having thus described my new variety of plum tree, I claim:

1. A new and distinct variety of plum tree, as described and illustrated, bearing clingstone fruit which ripens at approximately the same time as the Santa Rosa (unpatented) variety of plum tree to which it is most nearly similar, the fruit of the new variety being characterized as to novelty in relation to the fruit of the Santa Rosa variety in being larger, in having a more purplish and less reddish skin coloration, in having a form which is more narrowly ovoid rather than globose, in which the base is broader and flatter than rounded, in which the shoulders are slanted more toward the apex, in which the apex is a short rounded point rather than being depressed, in having a relatively longer ripening period, in having superior shipping and keeping qualities, and in having flesh which is substantially less acid and which attains a fully reddish coloration when relatively immature.

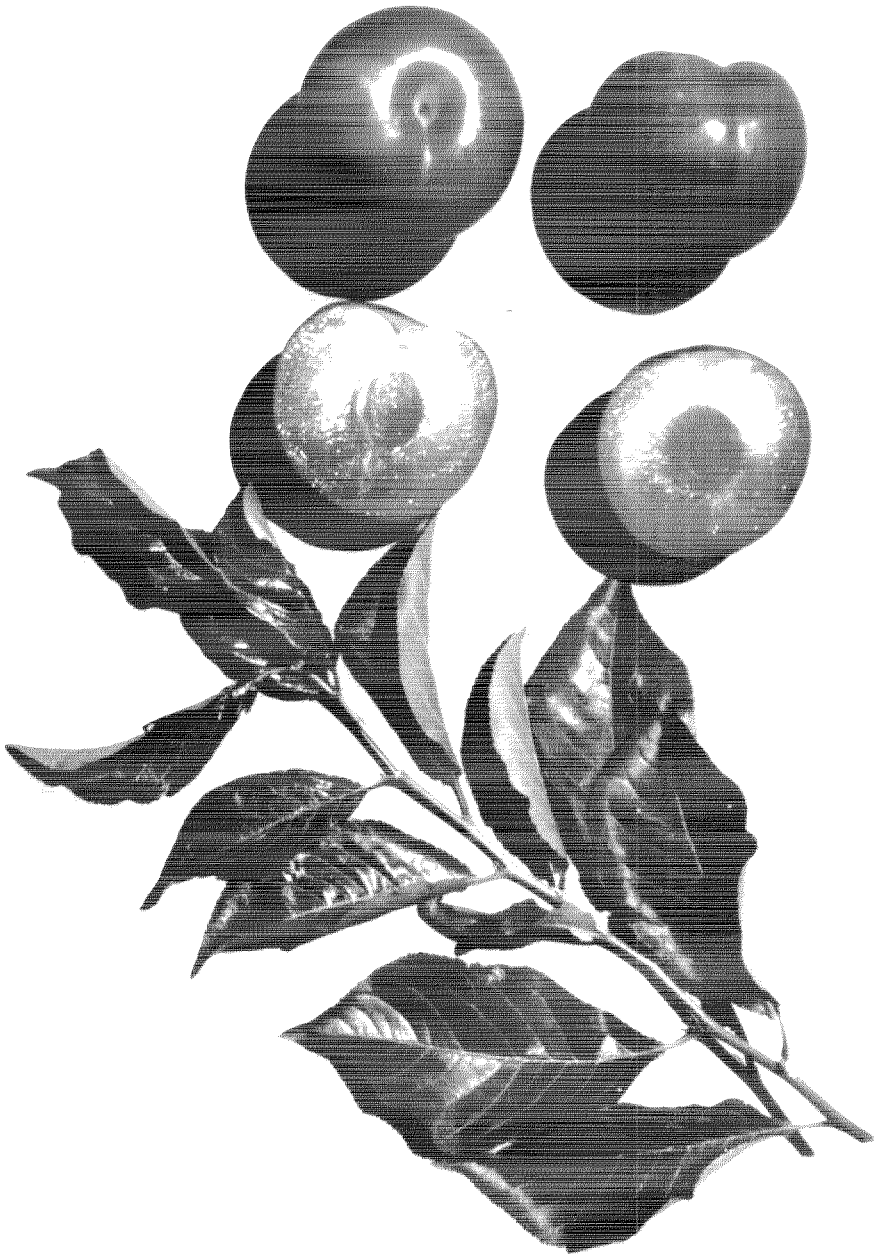

* * * * *